US012751644B2

(12) United States Patent
Schwartz et al.

(10) Patent No.: US 12,751,644 B2
(45) Date of Patent: Oct. 6, 2026

(54) SCANNING DEVICE WITH GEOMETRIC PATTERNS FOR CAMERA CALIBRATION

(71) Applicant: AETREX, INC., Teaneck, NJ (US)

(72) Inventors: Laurence I. Schwartz, New York, NY (US); Kumar Rajan, Teaneck, NJ (US)

(73) Assignee: AETREX, INC., Teaneck, NJ (US)

( * ) Notice: Subject to any disclaimer, the term of this patent is extended or adjusted under 35 U.S.C. 154(b) by 357 days.

(21) Appl. No.: 18/702,371

(22) PCT Filed: Oct. 25, 2022

(86) PCT No.: PCT/US2022/047660
§ 371 (c)(1),
(2) Date: Apr. 18, 2024

(87) PCT Pub. No.: WO2024/091223
PCT Pub. Date: May 2, 2024

(65) Prior Publication Data

US 2025/0248620 A1 Aug. 7, 2025

Related U.S. Application Data

(60) Provisional application No. 63/271,446, filed on Oct. 25, 2021.

(51) Int. Cl.
*G01B 11/25* (2006.01)
*A61B 5/107* (2006.01)

(52) U.S. Cl.
CPC ............ *A61B 5/1074* (2013.01); *G01B 11/25* (2013.01)

(58) Field of Classification Search
CPC .............................. A61B 5/1074; G01B 11/25
USPC ............................................................ 33/515
See application file for complete search history.

(56) References Cited

U.S. PATENT DOCUMENTS

| | | | | | |
|---|---|---|---|---|---|
| 5,689,446 | A * | 11/1997 | Sundman | A61B 5/1074 702/167 |
| 10,837,868 | B2 * | 11/2020 | Boffa | G01B 21/042 |
| 11,151,738 | B2 * | 10/2021 | Schwartz | A61B 5/1038 |
| 11,215,449 | B2 * | 1/2022 | Natori | G01B 11/2522 |
| 12,011,298 | B2 * | 6/2024 | Watts | A61B 5/70 |
| 2006/0034548 | A1 | 2/2006 | Pishdadian et al. | |
| 2012/0069193 | A1 | 3/2012 | Ramegowda et al. | |
| 2019/0236806 | A1 | 8/2019 | Jiang et al. | |
| 2021/0279900 | A1 | 9/2021 | Schwartz et al. | |
| 2024/0023639 | A1 * | 1/2024 | Liao | A43D 1/025 |
| 2024/0237916 | A1 * | 7/2024 | Ghaednia | A43D 1/02 |

FOREIGN PATENT DOCUMENTS

| | | | | |
|---|---|---|---|---|
| WO | WO-2018195096 A1 * | 10/2018 | H04N 23/90 |
| WO | WO-2023187181 A1 * | 10/2023 | H04N 13/254 |

OTHER PUBLICATIONS

International Search Report and Written Opinion of International Application No. PCT/US2022/047660 mailed Feb. 28, 2023, 14 pgs.

* cited by examiner

*Primary Examiner* — George B Bennett
(74) *Attorney, Agent, or Firm* — Lowenstein Sandler LLP

(57) ABSTRACT

Embodiments of the present disclosure relate to a scanning device comprising a support base, a calibration pattern disposed on an upper surface of the support base, and a plurality of cameras distributed around an outer perimeter of the support base. In at least one embodiment, the calibration pattern is undetectable or substantially undetectable to the human eye.

20 Claims, 11 Drawing Sheets

SCANNING DEVICE WITH GEOMETRIC PATTERNS FOR CAMERA CALIBRATION

CROSS-REFERENCE TO RELATED APPLICATION(S)

This application claims the benefit of priority of U.S. Provisional Patent Application No. 63/271,446, filed on Oct. 25, 2021, the disclosure of which is hereby incorporated by reference herein in its entirety.

TECHNICAL FIELD

The present disclosure relates to the field of customized orthotic devices, and more particularly, to scanning devices used in connection with the production of customized orthotic devices or recommendations of orthotic devices.

BACKGROUND

Foot problems and the corresponding costs associated with foot care are significant in the United States and elsewhere. In cases where the foot problem is debilitating for particular activities, a number of hours of work time can be lost. Foot problems can arise from medical conditions, work conditions requiring standing or walking, athletic activities, and the like. Thus, foot problems can develop from medical conditions, work activity, or leisure activity.

Pedorthics is the field concerned with the design, manufacture, fit, and modification of footwear, foot orthotics, and foot devices as prescribed to help relieve painful or disabling conditions of the foot. The goal of pedorthics is to provide protection and comfort to the consumer/patient, which has been achieved primarily by developing orthotic devices capable of reducing pressure at the greatest areas of impact. Recently, additive manufacturing technologies have been used to produce custom orthotic devices or insoles in lieu of traditional subtractive manufacturing techniques and injection molding. Techniques, such as pressure sensing or imaging, have been used to compute three-dimensional (3D) models of the foot, which serve as the basis for generating customized orthotic devices with additive manufacturing or suggesting recommended pre-fabricated orthotic devices.

SUMMARY

The following presents a simplified summary of various aspects of the present disclosure in order to provide a basic understanding of such aspects. This summary is not an extensive overview of the disclosure. It is intended to neither identify key or critical elements of the disclosure, nor delineate any scope of the particular embodiments of the disclosure or any scope of the claims. Its sole purpose is to present some concepts of the disclosure in a simplified form as a prelude to the more detailed description that is presented later.

In one aspect, a scanning device comprises: a support base comprising a substantially flat upper surface; a calibration pattern disposed on the upper surface and undetectable or substantially undetectable by wavelengths in the visible spectrum; a plurality of cameras distributed around an outer perimeter of the support base and substantially oriented toward a center of the support base to capture the calibration pattern; and a processing device operatively coupled to each of the plurality of cameras. In at least one embodiment, the processing device is configured to activate and receive data generated by each of the plurality of cameras.

In at least one embodiment, the calibration pattern comprises a plurality of circles.

In at least one embodiment, wherein one or more of the plurality of circles differ in diameter.

In at least one embodiment, the scanning device further comprises a pressure panel disposed on the upper surface of the support base.

In at least one embodiment, the scanning device further comprises: a foil layer disposed on the pressure panel. In at least one embodiment, the calibration pattern is incorporated into the foil layer.

In at least one embodiment, the plurality of cameras disposed around the outer perimeter of the support base are equidistant from the center of the pressure panel.

In at least one embodiment, the processing device is further operably coupled to the pressure panel. In at least one embodiment, the processing device is further configured to activate and receive data generated by the pressure panel.

In at least one embodiment, pressure panel comprises a plurality of pressure sensors arranged in a planar configuration.

In at least one embodiment, each of the plurality of pressure sensors, when the pressure panel is activated, are configured to generate signals representative of underfoot pressure when an individual's foot is in contact with the pressure panel, the signals collectively defining a two-dimensional pressure map of the individual's foot.

In at least one embodiment, the processing device is configured to generate a three-dimensional reconstruction of an individual's foot based on data captured by the pressure panel and each of the plurality of cameras when the individual's foot is in contact with the pressure panel.

In at least one embodiment, the processing device is configured to transmit data generated by the pressure panel and each of the plurality of cameras to a processing server for generating a three-dimensional reconstruction of the individual's foot and/or data descriptive of an orthotic device customized to the individual's anatomy.

In at least one embodiment, the outer perimeter of the support base is a circular perimeter.

In at least one embodiment, a total number of the plurality of cameras is four.

In at least one embodiment, the four cameras are unevenly distributed around the circular perimeter.

In at least one embodiment, at least one of the plurality of cameras comprises a depth sensor configured to capture depth data during image capture by its corresponding camera.

In another aspect, a method comprises: capturing, by each of a plurality of cameras, one or more calibration images of a calibration pattern disposed above a support base of a scanning device; calibrating each of the plurality of cameras based on the one or more calibration images; and capturing images of an individual's foot by the plurality of cameras arranged around the support base. In at least one embodiment, the calibration pattern is undetectable or substantially undetectable by wavelengths in the visible spectrum;

In at least one embodiment, the method further comprises computing a three-dimensional reconstruction of the individual's foot based at least partially on the images of the individual's foot.

In at least one embodiment, the one or more calibration images are infrared images.

In at least one embodiment, the calibration pattern comprises a plurality of circles.

In at least one embodiment, one or more of the plurality of circles differ in diameter.

In at least one embodiment, the support base comprises a pressure panel, and wherein the calibration pattern is part of a foil layer disposed on the pressure panel.

In at least one embodiment, the method further comprises capturing a two-dimensional pressure map of the individual's foot while the individual is standing on the pressure panel.

In at least one embodiment, the method further comprises: generating a three-dimensional reconstruction of the individual's foot based on the images of the individual's foot and the two-dimensional pressure map.

In another aspect, a system comprises the scanning device of any of the preceding embodiments configured to perform the method of any of the preceding embodiments.

In another aspect, a non-transitory computer-readable storage medium comprises instructions encoded thereon that, when executed by a processing device, cause the processing device to perform the method of any of the preceding embodiments.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be exemplary only.

DETAILED DESCRIPTION

Figure 1:
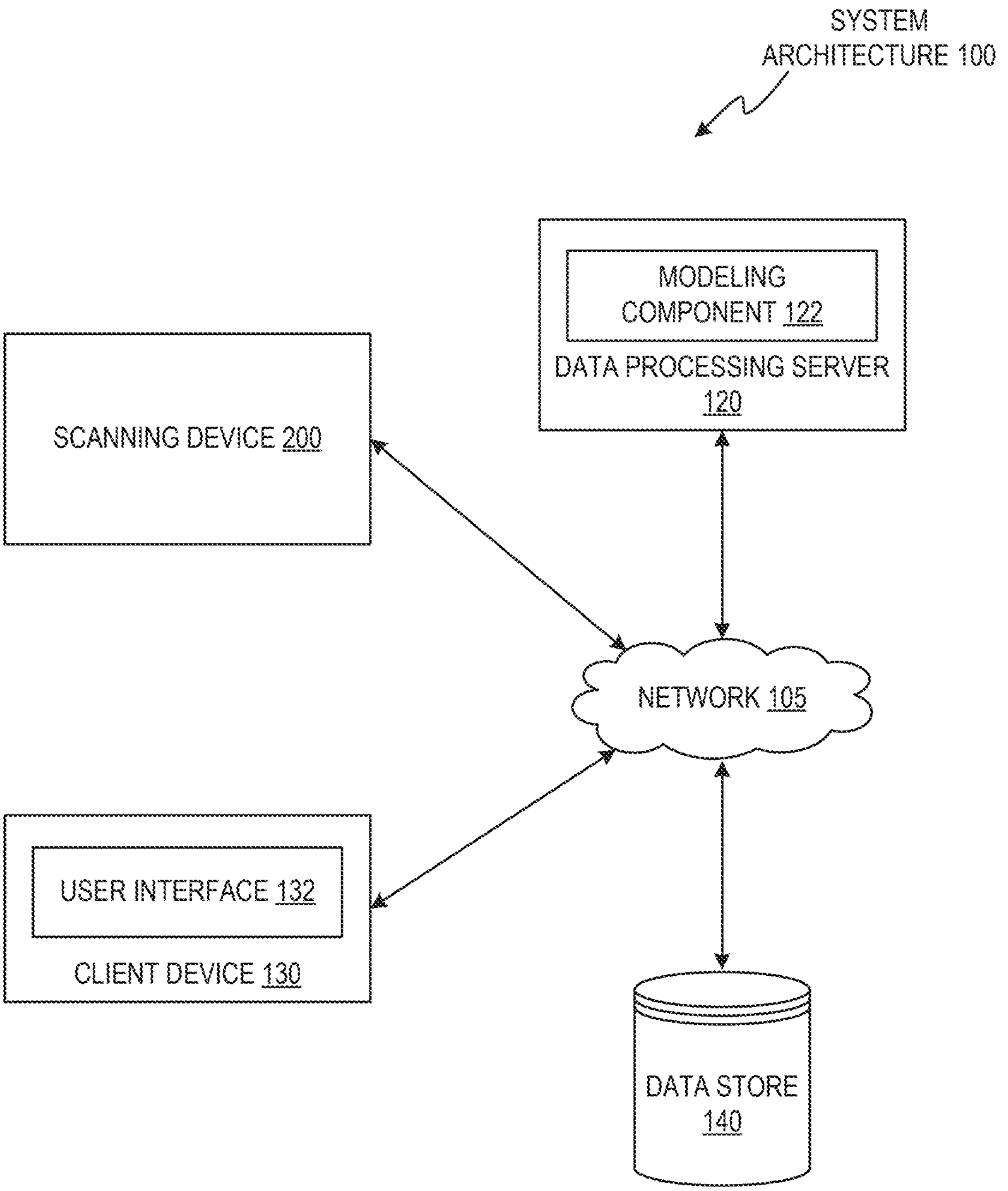
FIG. 1 illustrates an exemplary system architecture in accordance with embodiments of the present disclosure.

Described herein are embodiments of a scanning device capable of capturing images of the user's foot or feet from different angles with a plurality of cameras. In at least one embodiment, the scanning device includes, in addition to or in lieu of imaging functionality, the ability to capture two-dimensional pressure maps of an individual's foot or feet using a pressure panel.

In at least one embodiment, such as embodiments that utilize a pressure panel, the scanning device may comprise a foil layer with a camera calibration pattern (or simply a "calibration pattern") that is used by the plurality of cameras for calibration. The foil layer may, for example, be disposed on the pressure panel. As used herein, the terms "foil" and "foil layer" may refer to a thin material formed from one or more layers, and may include one or more layers of a deposited film, a paint, an ink, or other material. In some embodiments, the foil layer may include an outermost protective layer to prevent damage to underlying layers. In other embodiments, such as embodiments that do not utilize a pressure panel, the film, paint, ink, or other material may be disposed directly on a surface on which the user stands during operation of the scanning device with or without a protective layer.

In at least one embodiment, a deposited film, paint, ink, or other material may form a pattern (e.g., on a surface of the scanning device, on the foil, etc.), such as a plurality of circles, at fixed locations to facilitate self-calibration by the cameras. For example, certain embodiments utilize an ellipse fitting algorithm and a camera calibration algorithm based on geometric patterns (e.g., a geometric pattern painted onto the foil or directly onto a surface of the scanning device). In at least one embodiment, the pattern is formed using materials that are detectable in the infrared spectrum (e.g., greater than about 700 nm) and undetectable or substantially undetectable in the visible spectrum (i.e., undetectable or substantially undetectable by the human eye). As used herein, "substantially undetectable" means that the pattern may be very faintly visible to the human eye or to wavelengths less than 700 nm in the visible spectrum. Undetectable or substantially undetectable patterns include those produced using visibly opaque markings and coated with a material that is infrared-transparent or infrared-translucent, or patterns produced with markings formed from materials that are undetectable or substantially undetectable to visible light, with such materials being familiar to those of ordinary skill in the art.

In at least one embodiment, the scanning device may further be capable of enabling dynamic gait analysis by capturing a series of pressure maps of underfoot pressure when the individual steps onto and/or off of the scanning device. In at least one embodiment, the scanning device, or a separate device, performs a 3D reconstruction of the individual's foot or feet based on the pressure map (representative of the bottom of the foot) and the images captured at various angles (representative of the top, front, side, and back views of the foot).

In at least one embodiment, the cameras are evenly distributed around a perimeter of the scanning device. In at least one embodiment, the cameras are unevenly distributed. For example, in an embodiment where only four cameras are used, the cameras may be arranged to define the four corners of a rectangle while being oriented toward a center of the pressure panel (i.e., toward the individual's foot or feet).

In at least one embodiment, the scanning device may enable during gait analysis by capturing pressure data for the user's foot or feet, for example at 5-10 second intervals as the user steps into, across, and/or out of the scanning device. The data may be processed to generate a video showing the evolution of underfoot pressure over time.

Certain embodiments of the present disclosure are also directed to methods utilizing geometric partial differential equations to generate a 3D surface representative of a foot. The method can advantageously compute the 3D model using depth images obtained from the cameras in conjunction with an underfoot pressure map so as to account for the underside of the foot which is not visible to the cameras. Such methods are described in U.S. Pat. No. 11,151,738, the disclosure of which is hereby incorporated by reference herein in its entirety.

In the description that follows, reference is made to the analysis of an individual's feet for the purpose of generating orthotic devices. It is to be understood that the embodiments described herein are not limited to use in any one particular application and that changes may be made to the disclosed embodiments without departing from the spirit and scope of the disclosure. Although the present disclosure has been described herein in the context of foot orthotics, those of ordinary skill in the art will recognize that its usefulness is not limited thereto and that the present disclosure may be beneficially implemented in connection with the generation of orthotics for other body parts as well. Moreover, the embodiments described herein are not limited to measurements that require both imaging and pressure sensing. Embodiments utilizing imaging exclusively or pressure sensing exclusively are also contemplated. Thus, the embodiments described herein that incorporate both pressure sensing and imaging functionality are merely exemplary.

System Architecture

Exemplary implementations of the embodiments of the present disclosure are now described. FIG. 1 illustrates an exemplary system architecture 100, in accordance with embodiments of the present disclosure. The system architecture 100 includes a scanning device 200, a data processing server 120, a client device 130, and a data store 140, with each device of the system architecture 100 being communicatively coupled via a network 105. One or more of the devices of the system architecture 100 may be implemented using a generalized computer system 600, described with respect to FIG. 6. The devices of the system architecture 100 are merely illustrative, and it is to be understood that other scanning devices, user devices, data processing servers, data stores, and networks may be present.

In one embodiment, network 105 may include a public network (e.g., the Internet), a private network (e.g., a local area network (LAN) or wide area network (WAN)), a wired network (e.g., Ethernet network), a wireless network (e.g., an 802.11 network or a Wi-Fi network), a cellular network (e.g., a Long Term Evolution (LTE) network), routers, hubs, switches, server computers, and/or a combination thereof. Although the network 105 is depicted as a single network, the network 105 may include one or more networks operating as stand-alone networks or in cooperation with each other. The network 105 may utilize one or more protocols of one or more devices to which they are communicatively coupled.

In one embodiment, the scanning device 200 includes a support base comprising substantially flat upper and lower surfaces, a pressure panel disposed on the upper surface of the support base, and a plurality of cameras distributed around an outer perimeter of the support base and substantially oriented toward a center of the pressure panel. In at least one embodiment, the scanning device 200 further comprises an on-board processing device operatively coupled to the pressure panel and each of the plurality of cameras. The processing device may be configured to activate and receive data generated by the pressure panel and each of the plurality of cameras. An exemplary scanning device 200 is described in greater detail with respect to FIGS. 2A-2C.

In one embodiment, the data processing server 120 may include one or more computing devices (such as a rackmount server, a router computer, a server computer, a personal computer, a mainframe computer, a laptop computer, a tablet computer, a desktop computer, etc.), data stores (e.g., hard disks, memories, databases), networks, software components, and/or hardware components from which digital contents may be retrieved. In at least one embodiment, the data processing server 120 may be a server utilized by the scanning device 200, for example, to process generated scan data of an individual's anatomy. In at least one embodiment, additional data processing servers may be present. In at least one embodiment, the data processing server 120 utilizes a modeling component 122 to generate and reconstruct 3D model data from data received from the scanning device 200.

In one embodiment, the client device 130 may include a computing device such as a personal computer (PC), laptop, mobile phone, smart phone, tablet computer, netbook computer, etc. An individual user may be associated with (e.g., own and/or operate) the client device 130. As used herein, a "user" may be represented as a single individual. However, other embodiments of the present disclosure encompass a "user" being an entity controlled by a set of users and/or an automated source. For example, a set of individual users federated as a community in a company or government organization may be considered a "user." In at least one embodiment, the user is the individual who is the subject of scanning by the scanning device 200. In at least one embodiment, the user is an operator, technician, or physician who is conducting or assisting with the scan of another individual with the scanning device 200.

The client device 130 may utilize one or more local data stores, which may be internal or external devices, and may each include one or more of a short-term memory (e.g., random access memory), a cache, a drive (e.g., a hard drive), a flash drive, a database system, or another type of component or device capable of storing data. The local data stores may also include multiple storage components (e.g., multiple drives or multiple databases) that may also span multiple computing devices (e.g., multiple server computers). In at least one embodiment, the local data stores may be used for data back-up or archival purposes.

The client device 130 may implement a user interface 132, which may allow the client device 130 to send/receive information to/from other client devices, the scanning device 200, the data processing server 120, and the data store 140. The user interface 132 may be a graphical user interface (GUI). For example, the user interface 132 may be a web browser interface that can access, retrieve, present, and/or navigate content (e.g., web pages such as Hyper Text Markup Language (HTML) pages) provided by the data processing server 120. In one embodiment, the user interface 132 may be a standalone application (e.g., a mobile "app," etc.), that enables a user to use the client device 130 to send/receive information to/from other client devices, the scanning device 200, the data processing server 120, and the data store 140.

In one embodiment, the data store 140 may include one or more of a short-term memory (e.g., random access memory), a cache, a drive (e.g., a hard drive), a flash drive, a database system, or another type of component or device capable of storing data. The data store 140 may also include multiple storage components (e.g., multiple drives or multiple databases) that may also span multiple computing devices (e.g., multiple server computers). In at least one embodiment, the data store 140 may be cloud-based. One or more of the devices of system architecture 100 may utilize their own storage and/or the data store 140 to store public and private data, and the data store 140 may be configured to provide secure storage for private data. Such private data may include, for example, data descriptive of individuals who have been scanned with the scanning device 200, including names, contact information, physiological data, and scan data. In at least one embodiment, the data store 140 may be used for data back-up or archival purposes.

Although each of the scanning device 200, the data processing server 120, the client device 130, and the data store 140 are depicted in FIG. 1 as single, disparate components, these components may be implemented together in a single device or networked in various combinations of multiple different devices that operate together. In at least one embodiment, some or all of the functionality of the data processing server 120 and/or the data store 140 may be performed by the scanning device 200, the client device 130, or other devices. In an exemplary embodiment, the client device 130 may be within close proximity of or integrated with the scanning device 200, for example, as part of a scanning kiosk. In such embodiments, the client device 130 may implement the functionality of the modeling component 122, or may utilize the data processing server 120 to implement some or all of the functionality of the modeling component 122.

Scanning Device Embodiments

Figure 2A:
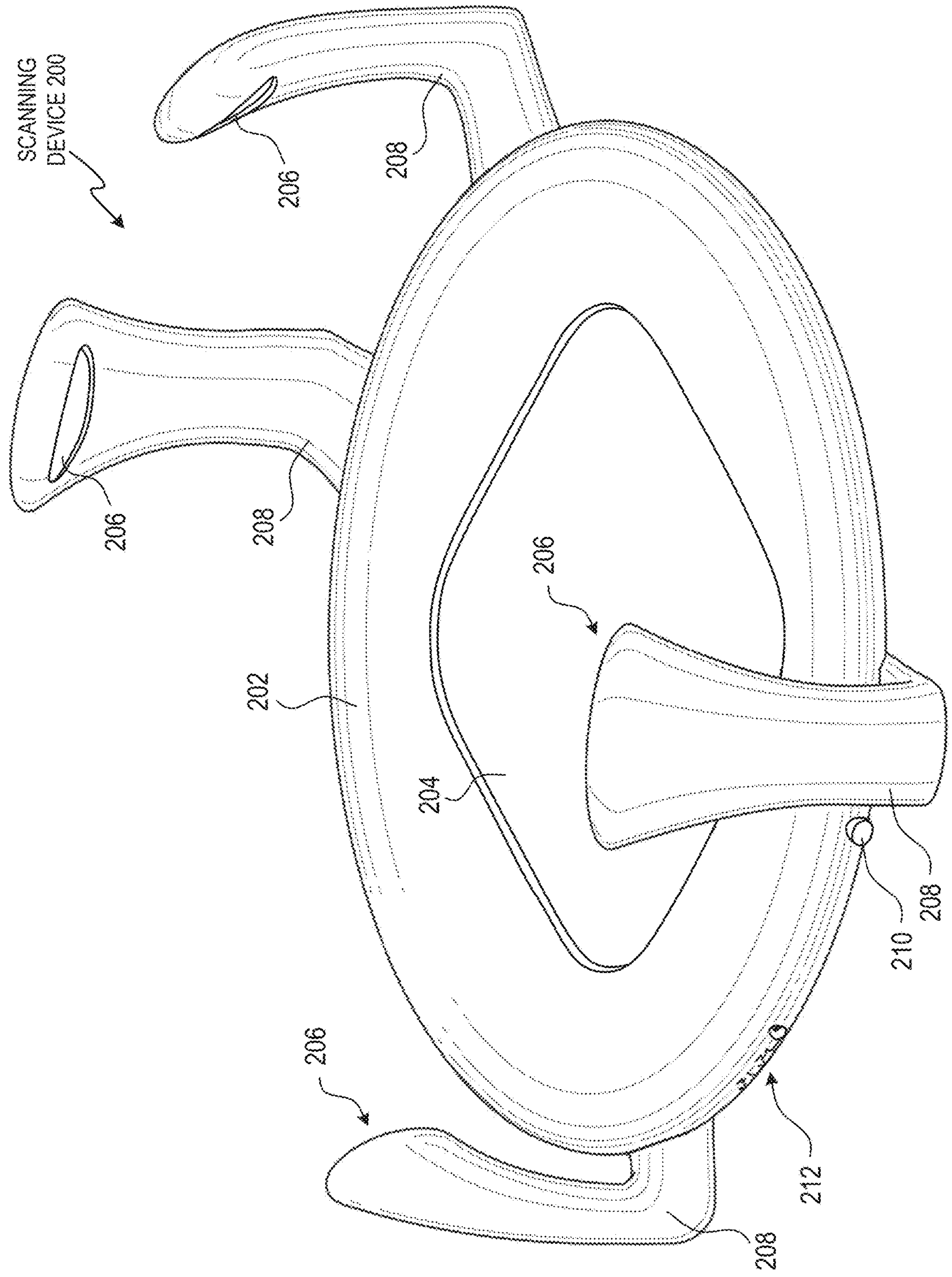
FIG. 2A shows a perspective view of an exemplary scanning device in accordance with embodiments of the present disclosure.
Figure 2B:
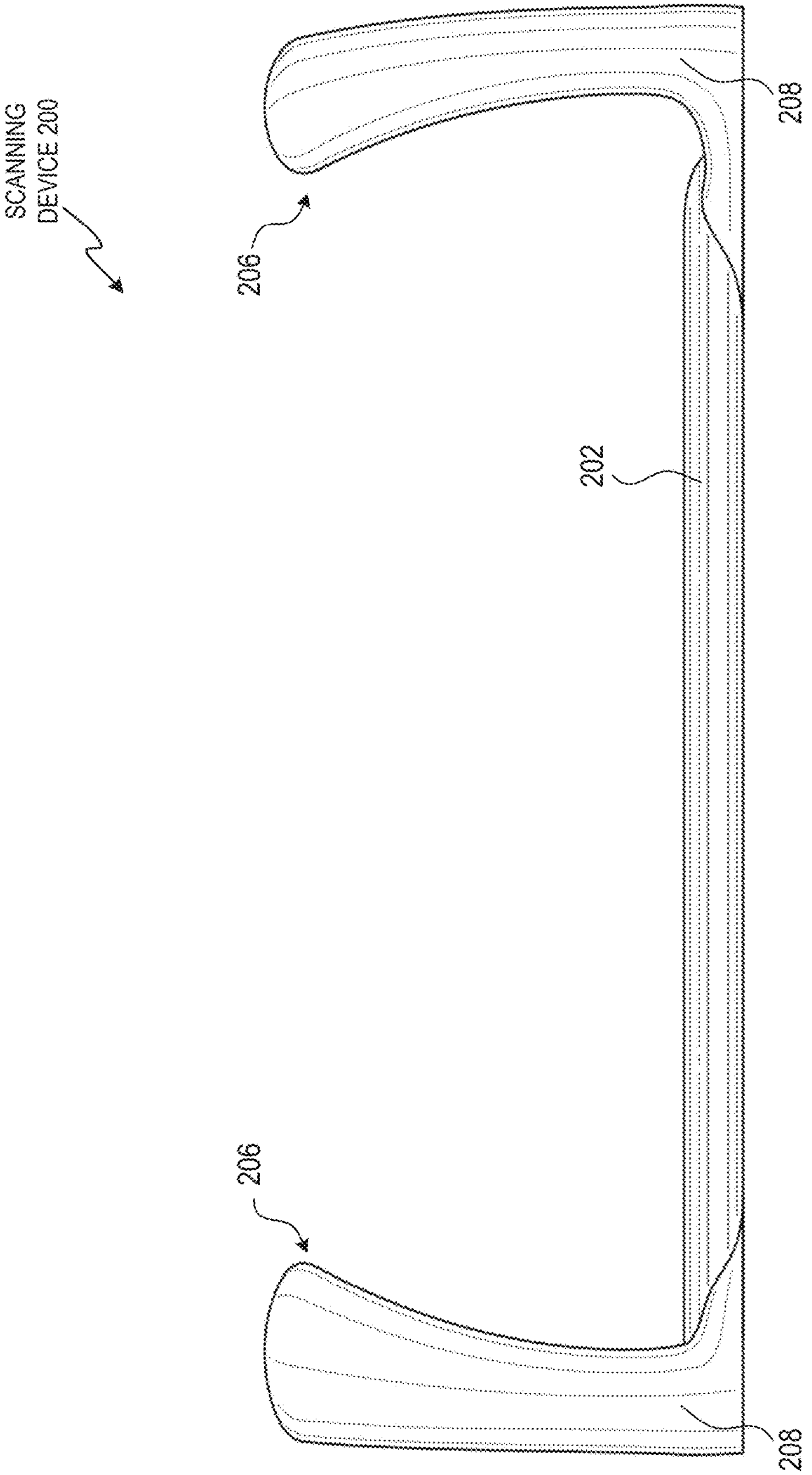
FIG. 2B shows a side view of the exemplary scanning device in accordance with embodiments of the present disclosure.
Figure 2C:
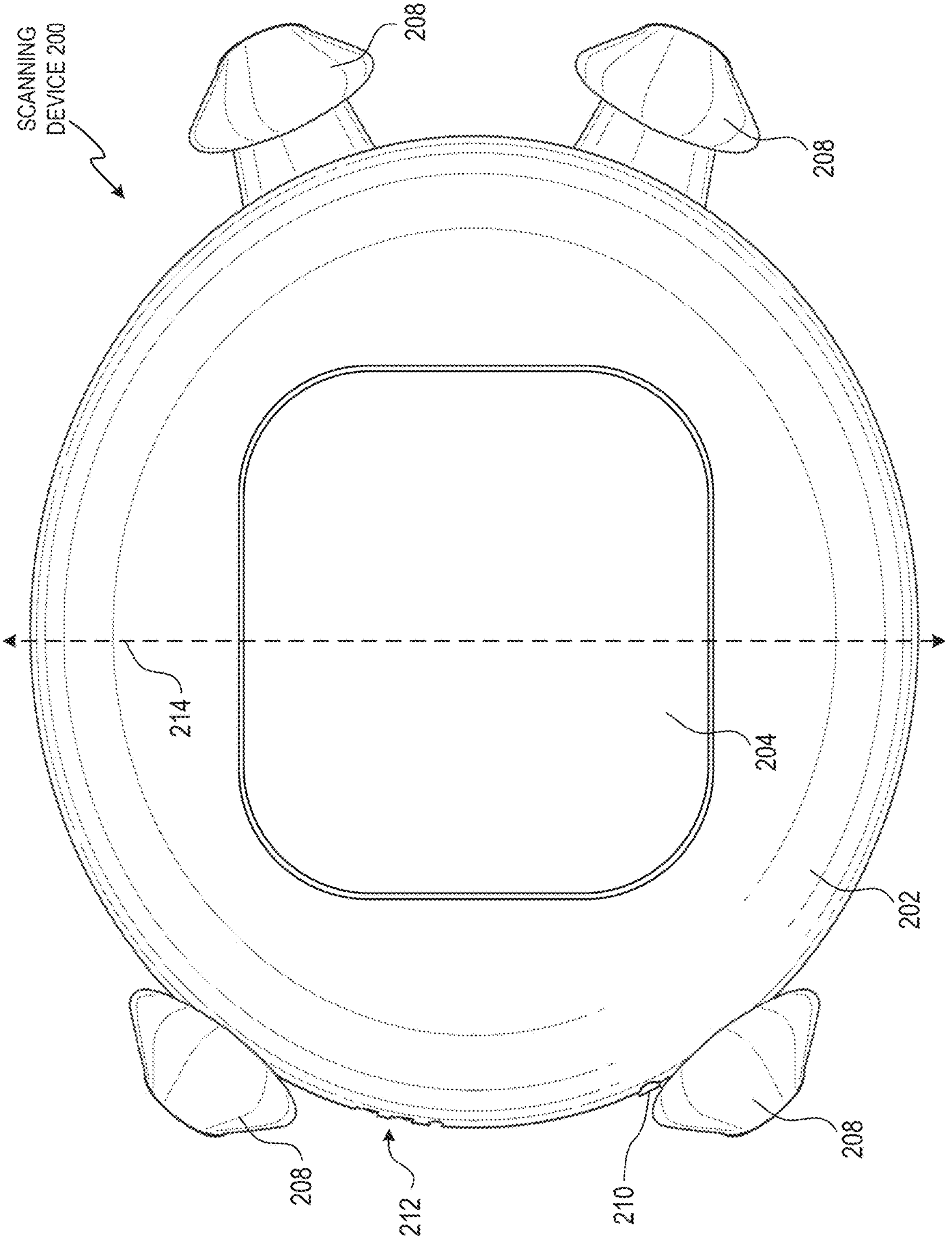
FIG. 2C shows a top view of the exemplary scanning device in accordance with embodiments of the present disclosure.

FIGS. 2A-2C show various views of the exemplary scanning device 200 in accordance with embodiments of the present disclosure. The scanning device 200 includes a support base 202, a pressure panel 204, and a plurality of cameras 206 distributed around the support base 202. Each camera 206 may be configured for capturing high-definition images (e.g., individual images or a movie), and may, in at least one embodiment, comprise an infrared sensor for capturing depth data. In at least one embodiment, one or more of the cameras 206 may be a stereo depth camera. The scanning device 200 may have one or more on-board processing devices that are operatively coupled to the cameras 206 and the pressure panel 204, and may transmit activation signals to the various components and control the timing at which signals are captured, collected, and transmitted to one or more external devices for processing (e.g., the data processing server 120, the client device 130, etc.).

In at least one embodiment, one or more of the cameras 206 are housed within or mechanically coupled to respective support arms 208. Each of the cameras 206 are mechanically coupled to or integrally formed with the support base via support arms 208, which may be substantially L-shaped, rigid members. In at least one embodiment, one or more of the support arms 208 are fixed in place, resulting in fixed, unmovable positions for the cameras 206. This may be beneficial in optimizing angles and distances at which images of the foot or feet are captured. In at least one embodiment, the positions of each camera 206 may be adjusted along the perimeter of the support base 202. For example, one or more of the support arms 208 may extend radially from the support base 202, and/or may be rotatable around a central axis of the support base 202 (e.g., slideably coupled to a track underneath the support base 202) and adjusted to a particular azimuthal angle. In at least one embodiment, one or more of the support arms 208 may be telescoping in order to adjust the vertical positions of their respective cameras 206 with respect to the support base 202.

In at least one embodiment, the cameras 206 may be positioned to define a walking path 214 across the support base 202, as illustrated in FIG. 2C. In the top view of FIG. 2C, the left-most and right-most support arms 208 may be horizontally separated by a distance (e.g., 24-36 inches) to allow for the individual to walk onto the support base 202 and pressure panel 204 either to enter the scanning device and prepare for a static scan, or to perform dynamic gait analysis. For example, to perform a static scan of both feet, the user may enter the scanning device from the bottom of FIG. 2C and rotate their feet/body by about 90 degrees. In at least one embodiment, the cameras 206 may be further separated to define an additional walking path (e.g., a walking path orthogonal to the walking path 214).

In at least one embodiment, the cameras 206 may be configured to rotate around the outer perimeter of the support base 202 to perform image capture at different angles with respect to the user's foot or feet. The scanning device 200 may include a motorized coupling mechanism that allows the support arms 208 to travel along a stationary track, or each of the support arms 208 may be coupled to a motorized track. The one or more cameras can be controlled such that images of the foot are captured at different angles as the cameras 206 traverse the track. In at least one embodiment, fewer than all of the cameras 206 shown are utilized, such as two or three cameras.

In at least one embodiment, the pressure panel 204 includes a plurality of pressure cells arranged in a planar configuration (e.g., arranged in rows and columns or in another arrangement) adapted for generating polychromatic foot pressure readings. In at least one embodiment, the pressure panel may be an iStep® Pressure Plate (Aetrex Worldwide, Inc.) or a variation thereof, which uses over 3,700 pressure sensors that each span an area of 0.25 $cm^2$. A method of generating a customized insole for footwear using information obtained from a pressure map of an individual's feet is described in U.S. Pat. No. 7,493,230, the disclosure of which is hereby incorporated by reference herein in its entirety. Functionality for performing pressure measurements and capturing images of an individual's feet and processing the captured data may be utilized similar to the descriptions in U.S. Pat. Nos. 9,402,567, 10,417,772, 10,463,257, and 10,492,712, the disclosures of which are hereby incorporated by reference herein in their entireties. In certain embodiments that do not utilize pressure sensing functionality, the pressure panel 204 may be replaced with a substantially flat surface, which may be integrally formed with the support base. A calibration pattern, as discussed in greater detail below, may be disposed directly on this substantially flat surface in certain embodiments.

In at least one embodiment, the support base 202 includes a power button/power indicator 210 for activating the scanning device 200. In at least one embodiment, the support base includes a panel 212, which may include a power input port and one or more ports for establishing a hard-wired connection with a client device (e.g., the client device 130) or a data processing server (e.g., the data processing server 120). In at least one embodiment, the scanning device 200 may be communicatively coupled to the client device or data processing server via a wireless connection.

In one embodiment, an exemplary process for performing a scan with the scanning device 200 comprises first performing a static scan of the individual's foot or feet. For example, the individual may be instructed (e.g., by a display screen operably coupled to the scanning device 200 or to an intermediate device, such as the client device 130 implementing the user interface 132) to step onto the pressure panel 204 with one foot or with both feet. In embodiments where the user steps onto the pressure panel 204 with one foot, the individual is then instructed to place the other foot by itself onto the pressure panel 204 after completion of a scan of the first foot. In at least one embodiment, the static scan comprises measuring an underfoot pressure of the individual's foot or feet by the pressure panel 204 and capturing images of and/or depth data for the individual's foot or feet by the cameras 206. After performing the static scan, the individual may be instructed to walk out of the scanning device 200 to perform a dynamic gait analysis by measuring a change in underfoot pressure over time during the individual's movement. In at least one embodiment, the user may be instructed to walk into and out of the scanning device 200, walk into the scanning device 200 and remain still, or walk out of the scanning device 200 from a static position. In at least one embodiment, the dynamic gait analysis is performed prior to performing the static scan.

Camera Calibration

Figure 3:
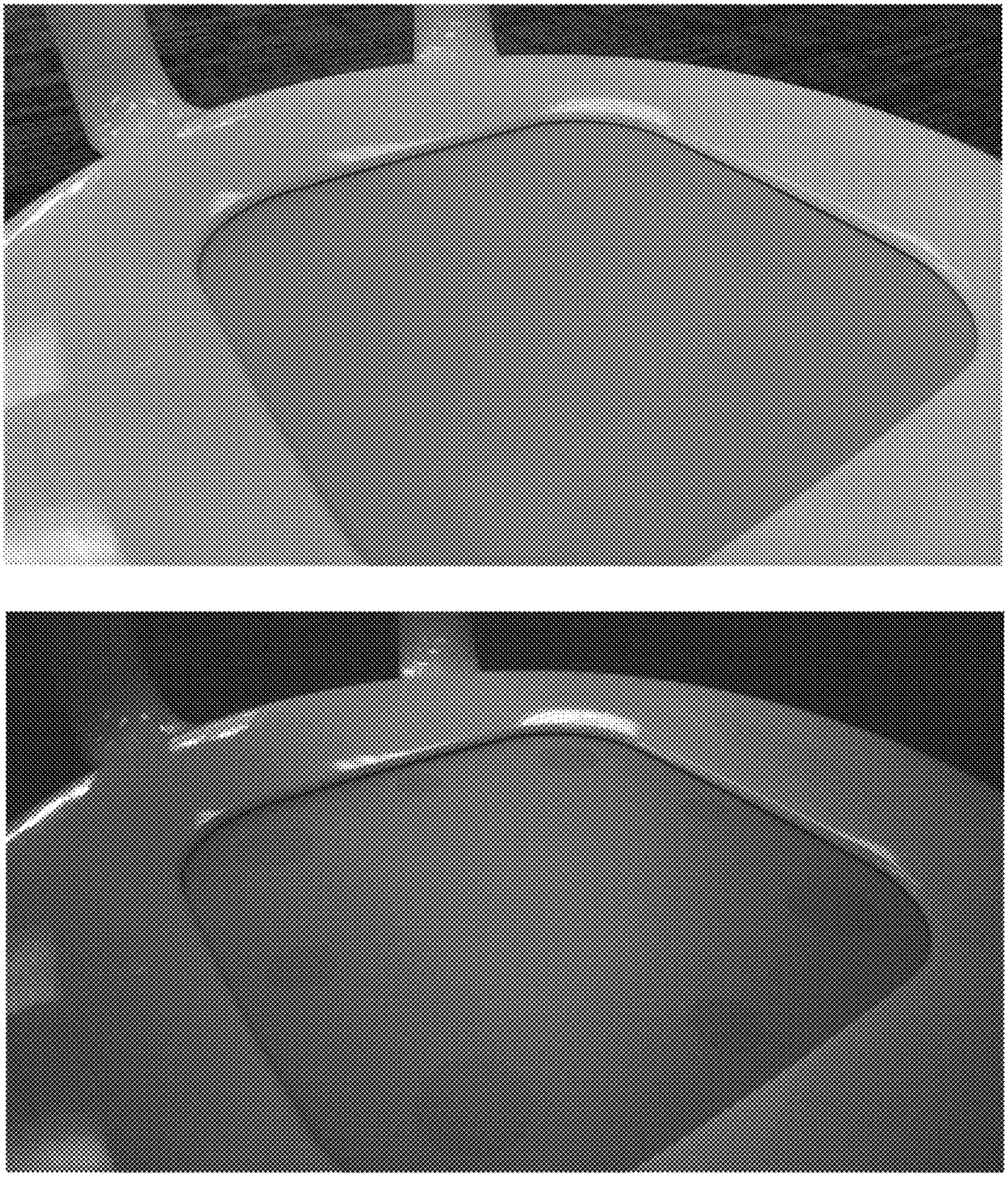
FIG. 3 shows an image of the scanner captured in the visible spectrum (top) compared to an image of the scanner captured in the infrared spectrum (2), revealing the calibration pattern along the top of the pressure panel in accordance with embodiments of the present disclosure.

FIG. 3 shows an image of the scanner captured in the visible spectrum (top) compared to an image of the scanner captured in the infrared spectrum (2), revealing the calibration pattern along the top of the pressure panel.

In at least one embodiment, the pattern of a foil layer is disposed onto an upper surface of the pressure panel using a paint/ink that is visible in the visible spectrum. The paint may be overlaid with a further layer of paint/ink that is opaque in the visible spectrum, but is transparent in the infrared spectrum (e.g., opaque to the human eye, but invisible to the cameras during the calibration process). The composition of the materials used in the foil layer may be any composition as appreciated by those of ordinary skill in the art.

Figure 4A:
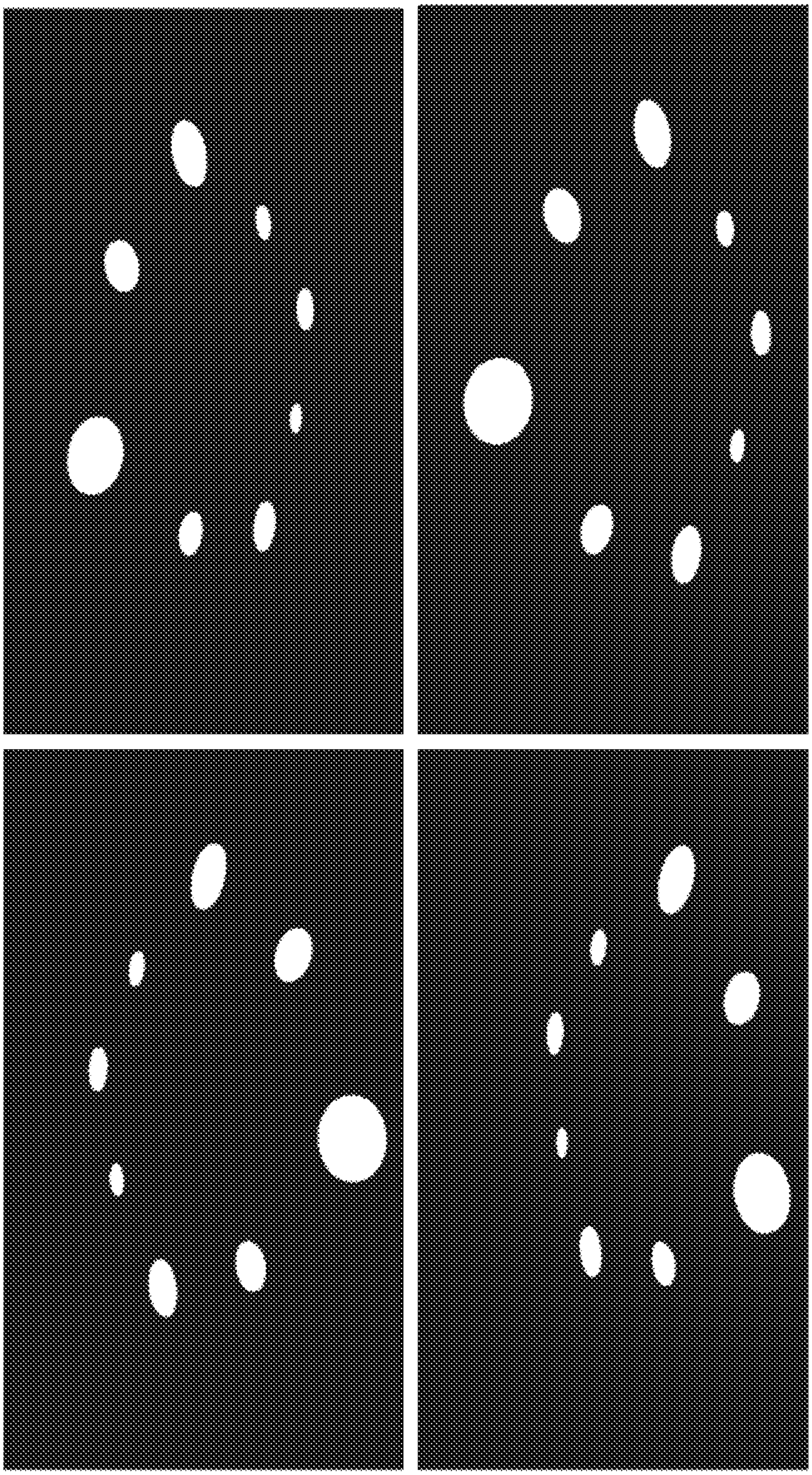
FIG. 4A illustrates pre-defined approximations for the geometric patterns to be identified within images captured by each camera in accordance with embodiments of the present disclosure.
Figure 4B:
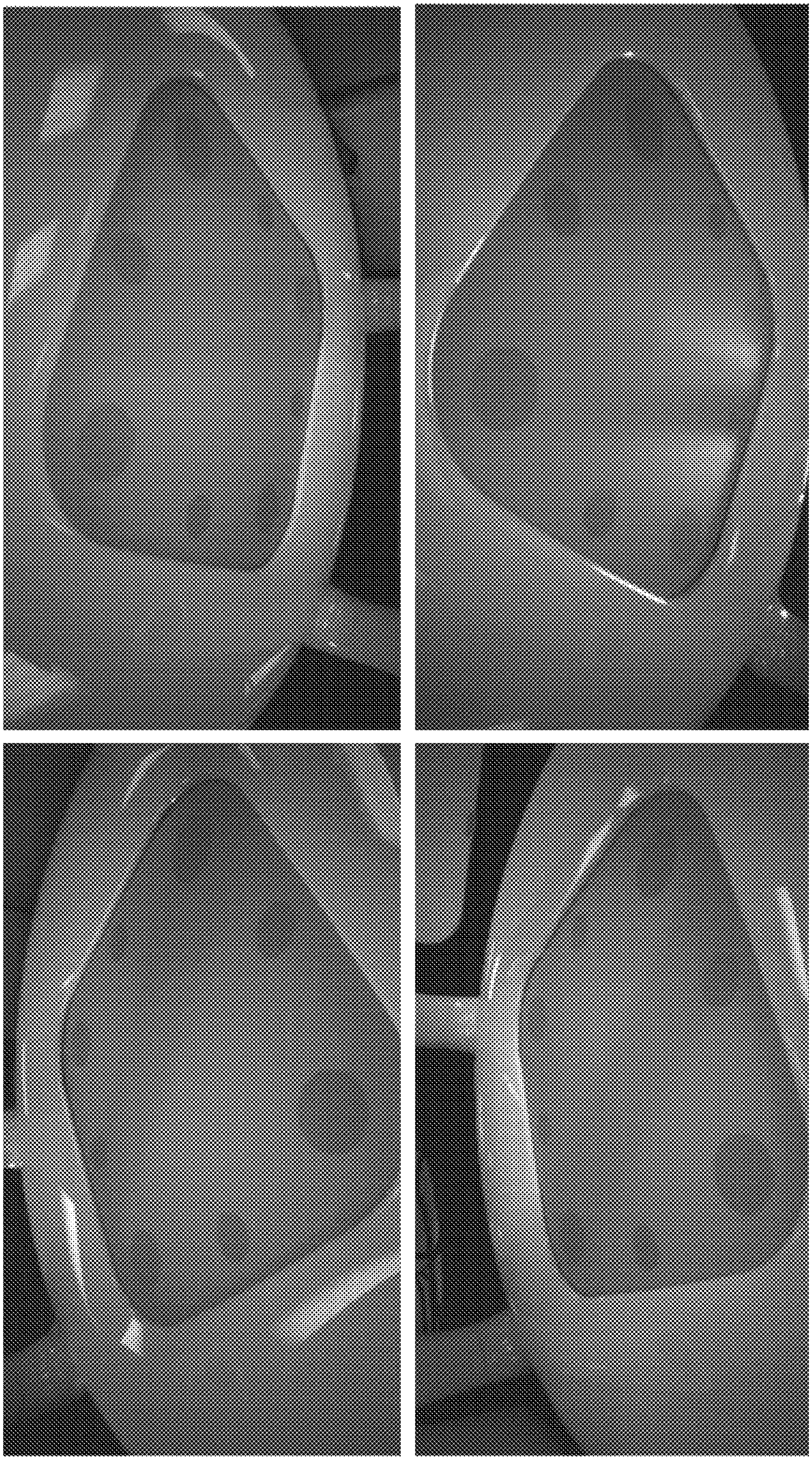
FIG. 4B shows infrared images captured by each camera from their respective vantage points in accordance with embodiments of the present disclosure.
Figure 4C:
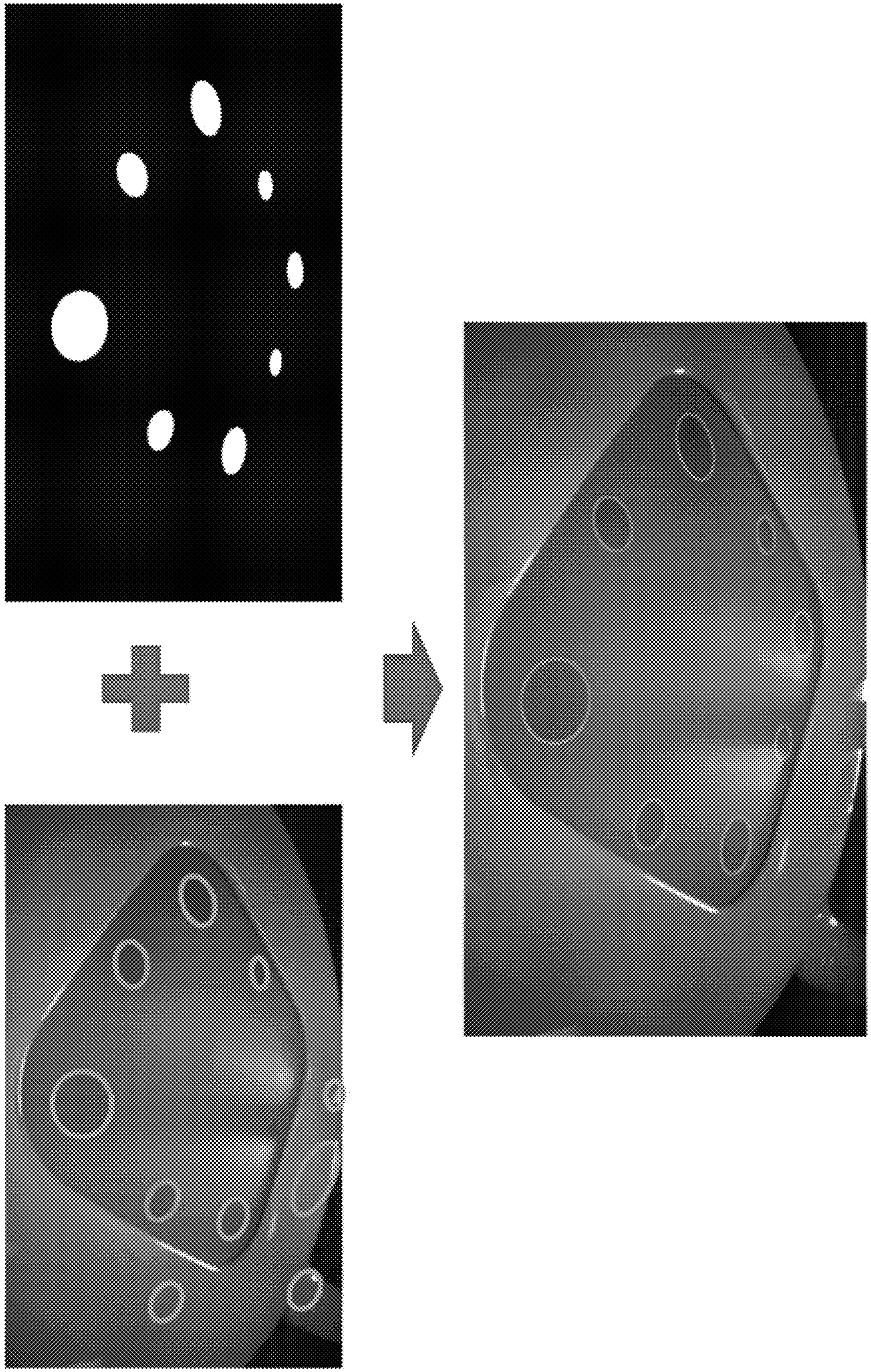
FIG. 4C illustrates ellipse fitting based on the calibration pattern in accordance with embodiments of the present disclosure.
Figure 4D:
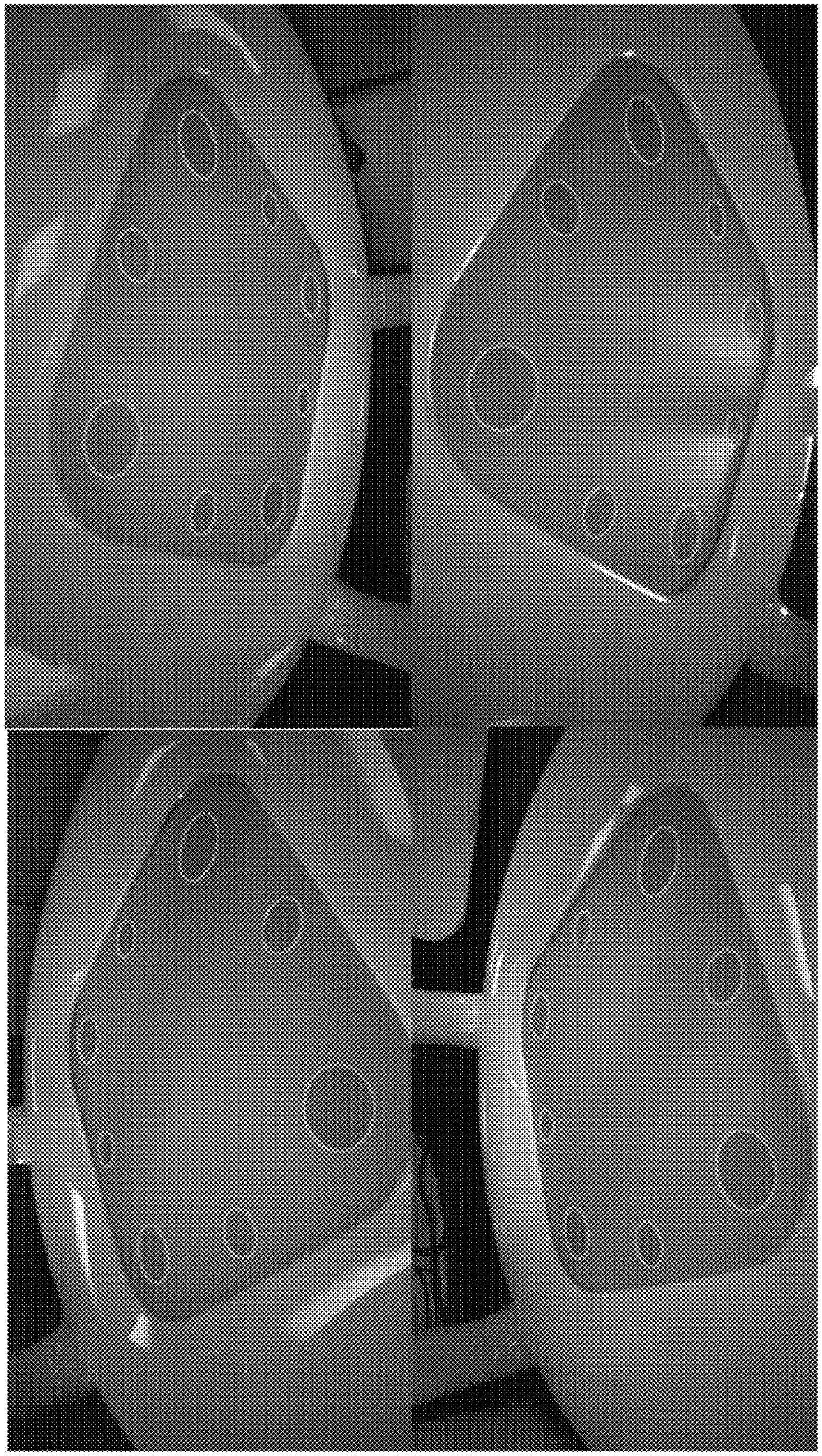
FIG. 4D illustrates detection of the final set of ellipses across all cameras in accordance with embodiments of the present disclosure.

In at least one embodiment, a camera calibration algorithm is performed as follows. First, a pre-defined approximation for the geometric pattern is identified for each camera (as illustrated in FIG. 4A). Next, each of the cameras captures an infrared image of the foil (as shown in FIG. 4B). For each camera image, an algorithm is utilized to find all possible ellipse candidates using an adaptive thresholding and ellipse-fitting method, which may utilized the pre-defined patterns identified in the first step as starting points for the fitting (as illustrated in FIG. 4C). The detected ellipses from all the cameras are reconciled to detect the final set of ellipses across all the cameras (as shown in FIG. 4D). The extrinsic parameters for each camera are then derived from the geometry of the identified ellipses.

Although FIGS. 4A-4D are illustrated for a scanning device with four cameras, these embodiments are applicable to scanning devices with an arbitrary number of cameras.

Figure 5:
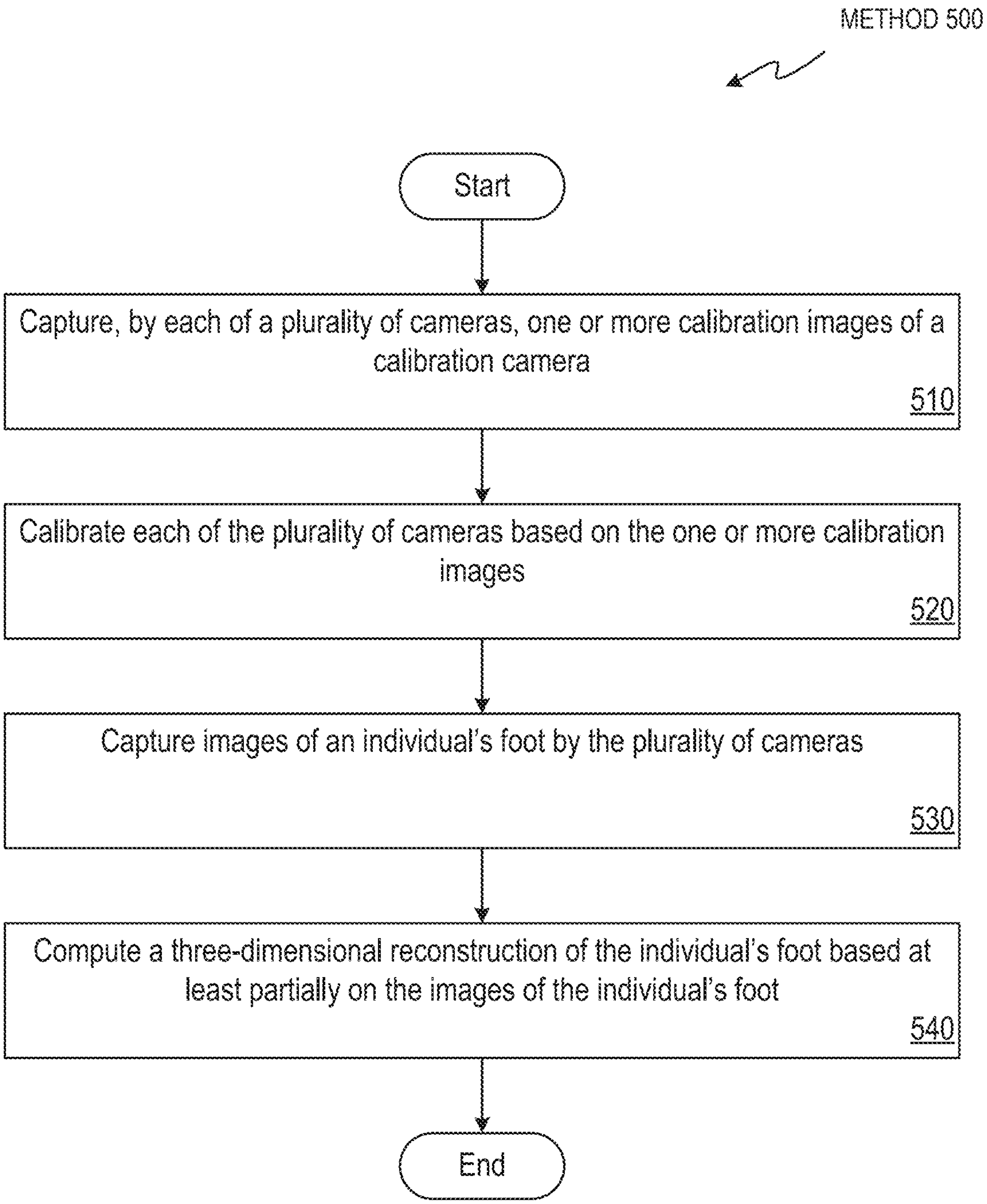
FIG. 5 is a flow diagram illustrating a method of scanning an individual's foot or feet in accordance with embodiments of the present disclosure.

FIG. 5 is a flow diagram illustrating a method 500 of scanning an individual's foot or feet in accordance with embodiments of the present disclosure. The method 500 may be performed by processing logic that includes hardware (e.g., circuitry, dedicated logic, programmable logic, microcode, etc.), software (e.g., instructions run on a processing device to perform hardware simulation), or a combination thereof. In at least one embodiment, the method 500 is performed by a processing device of the data processing server 120 implementing the modeling component 122, which transmits signals to the scanning device 200 to manage data capture. In at least one embodiment, some or all of the functionality of the modeling component 122 is distributed between the scanning device 200, the data processing server 120, and/or the client device 130.

The method 500 begins at block 510, the processing device causes each of a plurality of cameras (e.g., the cameras 206) to capture one or more calibration images of a calibration pattern disposed above a support base of a scanning device (e.g., the support base 202 of the scanning device 200). In at least one embodiment, the one or more calibration images are infrared images. In at least one embodiment, the pattern comprises a plurality of circles. In at least one embodiment, the plurality of circles differ in diameter. In at least one embodiment, the calibration pattern is part of a foil layer disposed on a pressure panel disposed on the support base.

At block 520, each of the plurality of cameras are calibrated based on the one or more calibration images.

At block 530, the processing device causes the plurality of cameras to capture images of the individual's foot (or feet) from different viewpoints around the support base. In at least one embodiment, the cameras configured to capture images comprising depth data.

At block 540, the processing device computes a three-dimensional reconstruction of the individual's foot based at least partially on the captured images.

In at least one embodiment, the processing device captures (e.g., directly by the scanning device 200 or by the scanning device 200 under the control of the data processing server 120) a two-dimensional pressure map of an individual's foot (or feet) while the individual is standing on a pressure panel (e.g., the pressure panel 204). In at least one embodiment, the three-dimensional reconstruction of the individual's foot is generated based further on the pressure map.

In at least one embodiment, the processing device generates data descriptive of an orthotic device based on the three-dimensional reconstruction of the individual's foot, for example, by generating a shape that matches an underfoot surface represented by the three-dimensional reconstruction. In at least one embodiment, the processing device generates a recommendation of a pre-made orthotic device based on various features represented by or derivable from the three-dimensional reconstruction (e.g., shoe size, arch height, heel width, or other features that would be appreciated by one of ordinary skill in the art). In at least one embodiment, the processing device transmits the data descriptive of the orthotic device to a manufacturing device to fabricate the orthotic device.

Exemplary Computer System Embodiments

Figure 6:
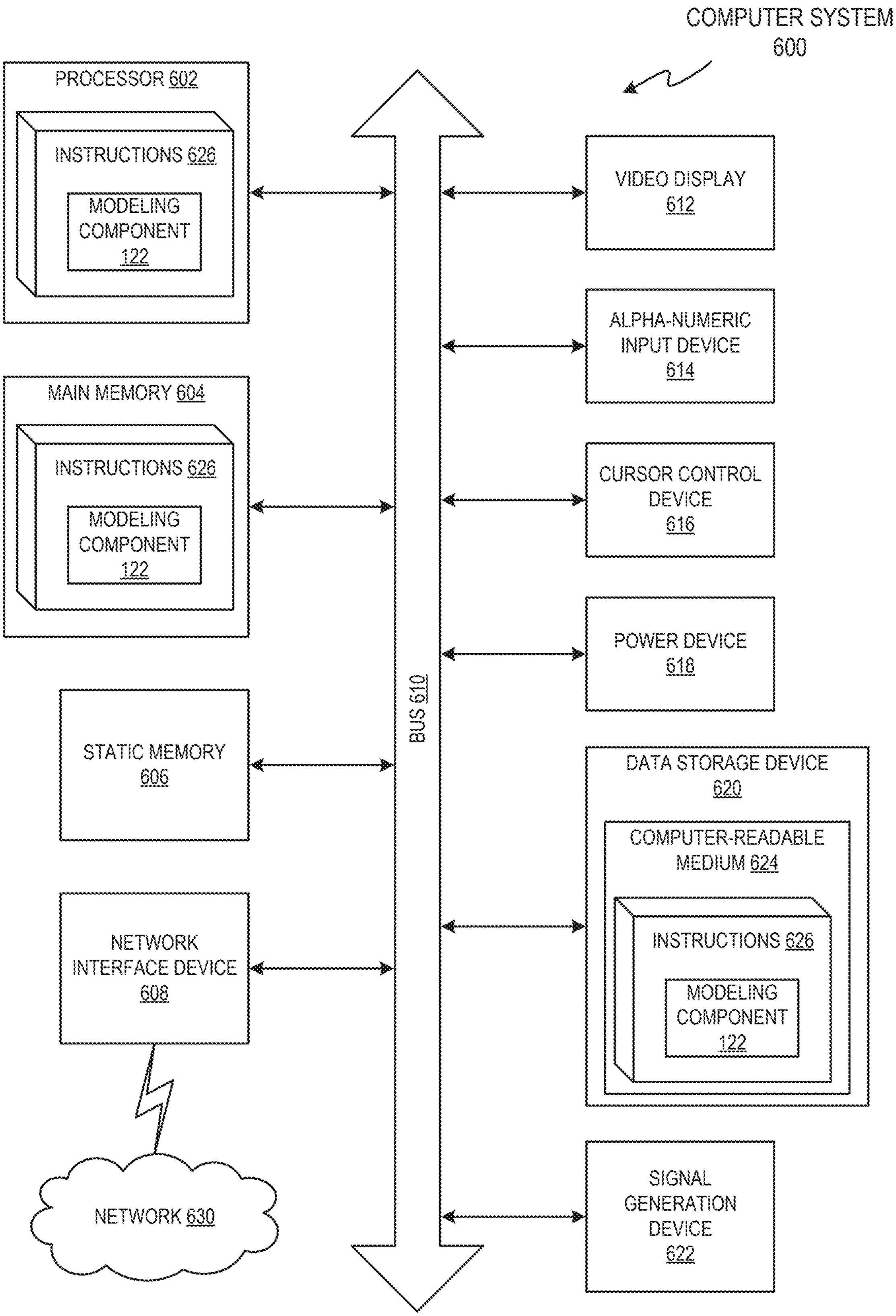
FIG. 6 is a block diagram illustrating an exemplary computer system for use in accordance with embodiments of the present disclosure.

FIG. 6 illustrates a diagrammatic representation of a machine in the exemplary form of a computer system 600 within which a set of instructions (e.g., for causing the machine to perform any one or more of the methodologies discussed herein) may be executed. In alternative embodiments, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine.

Further, while only a single machine is illustrated, the term "machine" shall also be taken to include any collection of machines that individually or jointly execute a set (or multiple sets) of instructions to perform any one or more of the methodologies discussed herein. Some or all of the components of the computer system 600 may be utilized by or illustrative of at least some of the devices of the system architecture 100, such as the scanning device 200, the data processing server 120, the client device 130, and the data store 140.

The exemplary computer system 600 includes a processing device (processor) 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a data storage device 620, which communicate with each other via a bus 610.

Processor 602 represents one or more general-purpose processing devices such as a microprocessor, central processing unit, or the like. More particularly, the processor 602 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 602 may also be one or more special-purpose processing devices such as an ASIC, a field programmable gate array (FPGA), a digital signal processor (DSP), network processor, or the like. The processor 602 is configured to execute instructions 626 for performing the operations and steps discussed herein, such as operations associated with the modeling component 122.

The computer system 600 may further include a network interface device 608. The computer system 600 also may include a video display unit 612 (e.g., a liquid crystal display (LCD), a cathode ray tube (CRT), or a touch screen), an alphanumeric input device 614 (e.g., a keyboard), a cursor control device 616 (e.g., a mouse), and/or a signal generation device 622 (e.g., a speaker).

Power device 618 may monitor a power level of a battery used to power the computer system 600 or one or more of its components. The power device 618 may provide one or more interfaces to provide an indication of a power level, a time window remaining prior to shutdown of computer system 600 or one or more of its components, a power consumption rate, an indicator of whether computer system is utilizing an external power source or battery power, and other power related information. In at least one embodiment, indications related to the power device 618 may be accessible remotely (e.g., accessible to a remote back-up management module via a network connection). In at least one embodiment, a battery utilized by the power device 618 may be an uninterruptable power supply (UPS) local to or remote from computer system 600. In such embodiments, the power device 618 may provide information about a power level of the UPS.

The data storage device 620 may include a computer-readable storage medium 624 on which is stored one or more sets of instructions 626 (e.g., software) embodying any one or more of the methodologies or functions described herein. The instructions 626 may also reside, completely or at least partially, within the main memory 604 and/or within the processor 602 during execution thereof by the computer system 600, the main memory 604 and the processor 602 also constituting computer-readable storage media. The instructions 626 may further be transmitted or received over a network 630 (e.g., the network 105) via the network interface device 608.

In one embodiment, the instructions 626 include instructions for operating or processing data generated by the scanning device 200, as described throughout this disclosure. While the computer-readable storage medium 624 is shown in an exemplary embodiment to be a single medium, the terms "computer-readable storage medium" or "machine-readable storage medium" should be taken to include a single medium or multiple media (e.g., a centralized or distributed database, and/or associated caches and servers) that store the one or more sets of instructions. The terms "computer-readable storage medium" or "machine-readable storage medium" shall also be taken to include any transitory or non-transitory medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description may have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is herein, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the preceding discussion, it is appreciated that throughout the description, discussions utilizing terms such as "configuring," "receiving," "converting," "causing," "streaming," "applying," "masking," "displaying," "retrieving," "transmitting," "computing," "generating," "adding," "subtracting," "multiplying," "dividing," "selecting," "parsing," "optimizing," "calibrating," "detecting," "storing," "performing," "analyzing," "determining," "enabling," "identifying," "modifying," "transforming," "aggregating," "extracting," "running," "scheduling," "processing," "capturing," "evolving," "fitting," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus, device, or system for performing the operations herein. This apparatus, device, or system may be specially constructed for the required purposes, or it may include a general purpose computer selectively activated or reconfigured by a computer program stored in the computer. Such a computer program may be stored in a computer- or machine-readable storage medium, such as, but not limited to, any type of disk including floppy disks, optical disks, compact disk read-only memories (CD-ROMs), and magnetic-optical disks, read-only memories (ROMs), random access memories (RAMs), EPROMs, EEPROMs, magnetic or optical cards, or any type of media suitable for storing electronic instructions.

The words “example” or “exemplary” are used herein to mean serving as an example, instance, or illustration. Any aspect or design described herein as “example” or “exemplary” is not necessarily to be construed as preferred or advantageous over other aspects or designs. Rather, use of the words “example” or “exemplary” is intended to present concepts in a concrete fashion. As used in this application, the term “or” is intended to mean an inclusive “or” rather than an exclusive “or.” That is, unless specified otherwise, or clear from context, “X includes A or B” is intended to mean any of the natural inclusive permutations. That is, if X includes A; X includes B; or X includes both A and B, then “X includes A or B” is satisfied under any of the foregoing instances. In addition, the articles “a” and “an” as used in this application and the appended claims should generally be construed to mean “one or more” unless specified otherwise or clear from context to be directed to a singular form. Reference throughout this specification to “certain embodiments,” “one embodiment,” “at least one embodiment,” or the like means that a particular feature, structure, or characteristic described in connection with the embodiment is included in at least one embodiment. Thus, the appearances of the phrase “certain embodiments,” “one embodiment,” “at least one embodiment,” or the like in various places throughout this specification are not necessarily all referring to the same embodiment.

The present disclosure is not to be limited in scope by the specific embodiments described herein. Indeed, other various embodiments of and modifications to the present disclosure, in addition to those described herein, will be apparent to those of ordinary skill in the art from the description and accompanying drawings. Thus, such other embodiments and modifications are intended to fall within the scope of the present disclosure. Further, while the present disclosure has been described in the context of a particular embodiment in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein, along with the full scope of equivalents to which such claims are entitled.

What is claimed is:

1. A scanning device comprising:

a support base comprising a substantially flat upper surface;

a calibration pattern disposed on the upper surface, wherein the calibration pattern is undetectable or substantially undetectable by wavelengths in the visible spectrum;

a plurality of cameras distributed around an outer perimeter of the support base and substantially oriented toward a center of the support base to capture the calibration pattern; and a processing device operatively coupled to each of the plurality of cameras, wherein the processing device is configured to activate and receive data generated by each of the plurality of cameras.

2. The scanning device of claim 1, wherein the calibration pattern comprises a plurality of circles.

3. The scanning device of claim 2, wherein one or more of the plurality of circles differ in diameter.

4. The scanning device of claim 1, further comprising:

a pressure panel disposed on the upper surface of the support base.

5. The scanning device of claim 4, further comprising:

a foil layer disposed on the pressure panel, wherein the calibration pattern is incorporated into the foil layer.

6. The scanning device of claim 4, wherein the plurality of cameras disposed around the outer perimeter of the support base are equidistant from the center of the pressure panel.

7. The scanning device of claim 4, wherein the processing device is further operably coupled to the pressure panel, and wherein the processing device is further configured to activate and receive data generated by the pressure panel.

8. The scanning device of claim 4, wherein the pressure panel comprises a plurality of pressure sensors arranged in a planar configuration.

9. The scanning device of claim 8, wherein each of the plurality of pressure sensors, when the pressure panel is activated, are configured to generate signals representative of underfoot pressure when an individual’s foot is in contact with the pressure panel, the signals collectively defining a two-dimensional pressure map of the individual’s foot.

10. The scanning device of claim 4, wherein the processing device is configured to generate a three-dimensional reconstruction of an individual’s foot based on data captured by the pressure panel and each of the plurality of cameras when the individual’s foot is in contact with the pressure panel.

11. The scanning device of claim 4, wherein the processing device is configured to transmit data generated by the pressure panel and each of the plurality of cameras to a processing server for generating a three-dimensional reconstruction of the individual’s foot and/or data descriptive of an orthotic device customized to the individual’s anatomy.

12. The scanning device of claim 1, wherein the outer perimeter of the support base is a circular perimeter.

13. The scanning device of claim 12, wherein a total number of the plurality of cameras is four.

14. The scanning device of claim 13, wherein the four cameras are unevenly distributed around the circular perimeter.

15. The scanning device of claim 1, wherein at least one of the plurality of cameras comprises a depth sensor configured to capture depth data during image capture by its corresponding camera.

16. A method comprising:

capturing, by each of a plurality of cameras, one or more calibration images of a calibration pattern disposed above a support base of a scanning device, wherein the calibration pattern is undetectable or substantially undetectable by wavelengths in the visible spectrum;

calibrating each of the plurality of cameras based on the one or more calibration images; and capturing images of an individual's foot by the plurality of cameras arranged around the support base.

17. The method of claim 16, further comprising:

computing a three-dimensional reconstruction of the individual's foot based at least partially on the images of the individual's foot.

18. The method of claim 16, wherein the one or more calibration images are infrared images.

19. The method of claim 16, wherein the calibration pattern comprises a plurality of circles, wherein one or more of the plurality of circles differ in diameter.

20. A non-transitory computer-readable storage medium having instructions encoded thereon that, when executed by a processing device, cause the processing device to perform a method comprising:

capturing, by each of a plurality of cameras, one or more calibration images of a calibration pattern disposed above a support base of a scanning device, wherein the calibration pattern is undetectable or substantially undetectable by wavelengths in the visible spectrum;

calibrating each of the plurality of cameras based on the one or more calibration images; and capturing images of an individual's foot by the plurality of cameras arranged around the support base.

* * * * *